United States Patent
Yamamoto

(10) Patent No.: US 8,691,040 B2
(45) Date of Patent: Apr. 8, 2014

(54) ABSORBER FORMING AND TRANSFERRING MECHANISM AND METHOD OF MANUFACTURING ABSORBENT ARTICLE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 160 days.

(21) Appl. No.: 12/743,993

(22) PCT Filed: Mar. 2, 2010

(86) PCT No.: PCT/JP2010/053735
§ 371 (c)(1),
(2), (4) Date: Mar. 7, 2011

(87) PCT Pub. No.: WO2010/101278
PCT Pub. Date: Sep. 10, 2010

(65) Prior Publication Data
US 2011/0303356 A1  Dec. 15, 2011

(30) Foreign Application Priority Data

Mar. 2, 2009 (JP) ............................... P2009-048402
Feb. 26, 2010 (JP) ............................... P2010-041922

(51) Int. Cl.
*A61F 13/15* (2006.01)
*B29C 65/00* (2006.01)
*B32B 37/00* (2006.01)
*B21D 39/03* (2006.01)
*B23P 11/00* (2006.01)
*B23P 19/00* (2006.01)

(52) U.S. Cl.
USPC ................ 156/276; 29/428; 29/700; 156/226

(58) Field of Classification Search
USPC .............................. 29/428, 700; 156/226, 276
See application file for complete search history.

(56) References Cited

U.S. PATENT DOCUMENTS

| 6,652,798 B1 | 11/2003 | Edvardsson |
| 2002/0153634 A1 | 10/2002 | Kugler et al. |
| 2003/0084767 A1 | 5/2003 | Tanaka et al. |
| 2004/0112508 A1 | 6/2004 | Umebayashi et al. |

FOREIGN PATENT DOCUMENTS

| CN | 1415277 A | 5/2003 |
| EP | 0151033 A2 | 8/1985 |
| EP | 1308147 A2 | 5/2003 |
| EP | 2308432 A1 | 4/2011 |

(Continued)

OTHER PUBLICATIONS

Office Action corresponding to CO 11-126455, dated Aug. 21, 2012.

(Continued)

*Primary Examiner* — Michael Orlando
(74) *Attorney, Agent, or Firm* — Lowe Hauptman & Ham, LLP

(57) ABSTRACT

In the absorber forming and transferring mechanism 100, at a core reception time, the rotational velocity $V_4$ of the rotary transfer member 160 is same as the rotation velocity $V_3$ of the forming drum 150. At a core transfer time, the rotational velocity $V_5$ of the rotary transfer member 160 is same as the conveyance velocity $V_2$ of the web 9A. During a period from the core reception time to the core transfer time, the rotational velocity $V_5$ of the rotary transfer member 160 becomes higher than the rotational velocity $V_3$ of the forming drum 150. During a period from the core transfer time to the core reception time, the rotational velocity $V_5$ of the rotary transfer member 160 becomes lower than the conveyance velocity $V_2$ of the web 9A.

15 Claims, 7 Drawing Sheets

(56) References Cited

FOREIGN PATENT DOCUMENTS

| | | |
|---|---|---|
| JP | 07150456 | 6/1995 |
| JP | 2002-516191 A | 6/2002 |
| JP | 2002516191 | 6/2002 |
| JP | 2003-199790 A | 7/2003 |
| JP | 2003199790 | 7/2003 |
| JP | 2005304815 | 11/2005 |
| JP | 2008-154964 A | 7/2008 |
| JP | 4133773 | 8/2008 |
| JP | 2008246137 | 10/2008 |
| JP | 2008246138 | 10/2008 |

OTHER PUBLICATIONS

Office Action corresponding to CL 2139-2011.

International Search Report for PCT/JP2010/053735 mailed Jun. 15, 2010.

Office Action (English) for corresponding Chinese Application No. 201080010134.1 issued Feb. 5, 2013.

Office Action issued Apr. 26, 2013 corresponds to Colombian patent application No. 11-126455.

Office Action issued May 14, 2013 corresponds to EA patent application No. 201101218.

Extended European Search Report issued May 14, 2013 corresponds to EP Patent application No. 10748869.4.

Office Action mailed Aug. 13, 2013, corresponds to Japanese patent application No. 2010-041922.

Office Action dated Sep. 18, 2013, corresponds to Colombian patent application No. 11-126455.

Office Action dated Nov. 20, 2013, corresponds to Mexican patent application No. MX/a/2011/009134.

Office Action dated Nov. 28, 2013, corresponds to Eurasian patent application No. 201101218/31.

ABSORBER FORMING AND TRANSFERRING MECHANISM AND METHOD OF MANUFACTURING ABSORBENT ARTICLE

RELATED APPLICATIONS

The present application is national phase of PCT/JP2010/053735 filed Mar. 2, 2010, and claims priority from Japanese Application Number 2009-048402, filed Mar. 2, 2009 and Japanese Application Number 2010-041922, filed Feb. 26, 2010, the disclosures of which are hereby incorporated by reference herein in their entirety.

TECHNICAL FIELD

The present disclosure relates to an absorber forming and transferring mechanism, and to a method of manufacturing an absorbent article.

BACKGROUND ART

An absorbent article, such as a disposable diaper and a sanitary napkin, has an absorber for absorbing body fluid discharged by a wearer. Generally, the absorber is formed of an absorber core made of ground pulp, superabsorbent polymer (SAP), and the like, and of a cover material that is made of tissue and the like and that covers the absorber core (see PTL 1, for example).

Specifically, in a manufacturing process of the absorber, firstly, ground pulp is prepared by grinding a pulp sheet with a grinder. Subsequently, the ground pulp is mixed with superabsorbent polymer while passing through a supply duct, and thereby a powder mixture is formed.

A drum-type absorber forming and transferring mechanism collects the powder mixture to form absorber cores, and then places the absorber cores at predetermined intervals on a first web being conveyed and including cover materials. A second web including further cover materials is placed on the web having the absorber cores placed thereon.

Thereafter, a continuous absorber web formed of the first and second webs with the absorber cores interposed therebetween is cut in the cross direction (CD) perpendicular to the conveyance direction (machine direction MD) of the absorber web, and thereby the absorbers are manufactured.

Forming recesses are made at predetermined intervals on the outer circumferential surface of the absorber forming and transferring mechanism. The forming recesses collect the powder mixture constantly blown out from a blowing device and thus form the absorber cores. A bottom portion of each of the forming recesses is provided with multiple suction holes attracting the powder mixture.

The inventors have discovered that when the powder mixture is constantly blown out from the blowing device, it adheres to portions other than the forming recesses (such as convex portions) on the outer circumferential surface of the absorber forming and transferring mechanism. As a result, a certain amount of the powder mixture is wasted, and thereby the cost of manufacturing the absorbers is increased.

To reduce the waste of the powder mixture, it is considered to narrow intervals between the multiple forming recesses formed in the outer circumferential surface of the absorber forming and transferring mechanism. However, if the intervals between the multiple forming recesses are narrowed, the intervals between the absorber cores placed on the web are also narrowed.

In contrast, in order to place the absorber cores at predetermined intervals on the web, the intervals between the multiple forming recesses formed in the outer circumferential surface of the absorber forming and transferring mechanism (i.e., the size of each convex portion) need to be widened. Therefore, a certain amount of the powder mixture is inevitably wasted.

CITATION LIST

Patent Literature

PTL 1: Japanese Patent Application Publication No. Hei 7-150456 (pp. 2 and 3, FIG. 1)

SUMMARY

It is desirable to provide an absorber forming and transferring mechanism and a method of manufacturing absorbent articles, which allow a predetermined interval between absorber cores placed on a web to be appropriately set for cost saving purposes.

A aspect of the present invention provides an absorber forming and transferring mechanism used for manufacturing an absorber formed of an absorber core and a cover material covering the absorber core, and configured to form the absorber core from powder and to place the absorber cores at predetermined intervals on a web including a continuum of the cover materials, the absorber forming and transferring mechanism comprising; a forming drum having forming recesses made at predetermined intervals, and configured to form the absorber cores by collecting the powder; a rotary transfer member configured to receive from the forming drum the absorber core formed by the forming drum, and to thereby transfer the absorber core received from the forming drum onto the web; a controller for controlling a rotational velocity of the rotary transfer member at the core reception time and at the core transfer time in accordance with velocities of the forming drum and the traveling web, respectively.

According to the aspects of the present invention, provided is the absorber forming and transferring mechanism and a method of manufacturing an absorbent article, which allow a predetermined interval between absorber cores placed on a web to be appropriately set in a case where the absorber cores are placed on the web at the predetermined intervals and achieve saving cost for manufacturing an absorber.

DETAILED DESCRIPTION

Hereinafter, an absorber forming and transferring mechanism and a method of manufacturing an absorbent article according to one or more embodiments of the present invention will be described with reference to the accompanying drawings. Note that, in the following description of the drawings, same reference signs denote same elements and portions. In addition, it should be noted that the drawings are schematic and are not to scale unless otherwise specified. Therefore, specific dimensions and the like should be determined in consideration of the following description. Moreover, the drawings do not necessarily reflect the real-life dimensional relationships and ratios of components.

Firstly, a configuration of an absorbent article 1 according to one or more embodiments will be explained with reference to FIG. 1 which is a partially cutaway perspective view of the absorbent article 1. In this particularly illustrated embodiment, the absorbent article 1 is a disposable pants-type diaper for adults.

Figure 1:
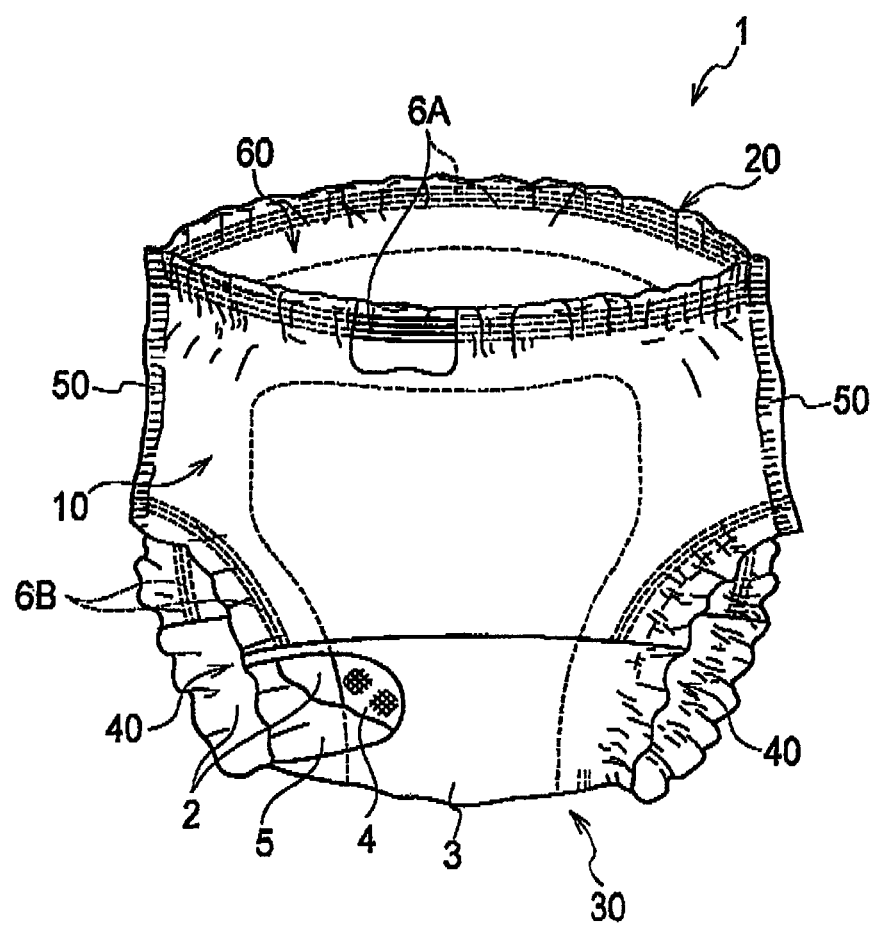
FIG. 1 is a partially cutaway, perspective view of an absorbent article according to one or more embodiments.

As shown in FIG. 1, the absorbent article 1 mainly includes a top sheet 2, a back sheet 3, an absorber 4 and a waterproof sheet 5.

The top sheet 2 is adapted to come into contact with the skin of a person to wear the absorbent article 1 (hereinafter, "wearer"). The top sheet 2 is made of a liquid permeable sheet such as a nonwoven fabric or a perforated plastic film. The back sheet 3 is provided outside the top sheet 2 (on a side facing away from the wearer). The back sheet 3 is made of a nonwoven fabric or the like.

The absorber 4 is provided between the top sheet 2 and the back sheet 3, for absorbing excretion discharged from the wearer. The absorber 4 is made of a mixture of ground pulp and superabsorbent polymer particles, or the like. The waterproof sheet 5 is provided between the back sheet 3 and the absorber 4, for blocking the permeation of the excretion from the wearer to the outside of the absorbent article 1. The waterproof sheet 5 is made of a liquid impermeable sheet.

The absorbent article 1 is provided with the top sheet 2, the absorber 4, the waterproof sheet 5 and the back sheet 3 in order, from the skin side of the wearer.

The absorbent article 1 thus configured includes, in combination, a front waistline portion 10 to be fitted to the front waist of a wearer, a back waistline portion 20 to be fitted to the back waist of the wearer, and a crotch portion 30 to be fitted to the crotch of the wearer. Incidentally, leg-surrounding openings 40 into which the legs of the wearer are inserted are formed at both sides of the crotch portion 30.

The front waistline portion 10 and the back waistline portion 20 are joined together by joint portions 50, and thereby form a waist opening to be fit around the body of the wearer. A waist gather 6A made of a stretchable rubber strand or the like is provided to an entire peripheral edge of the front waistline portion 10 and the back waistline portion 20.

For example, to make the front waistline portion 10 and the back waistline portion 20 stretchable in the cross direction perpendicular to the front-to-back direction from the front waistline portion 10 toward the back waistline portion 20, the front waistline portion 10 and the back waistline portion 20 may be provided with the waist gather 6A, or may themselves be made of a stretchable sheet.

The crotch portion 30 is provided between the front waistline portion 10 and the back waistline portion 20. Leg gathers 6B made of stretchable rubber strands or the like are provided on both sides of the crotch portion 30.

For example, to make the crotch portion 30 stretchable in the leg-encircling direction of the absorbent article 1, the crotch portion 30 may be provided with the leg gathers 6B, or may itself be made of a stretchable sheet.

Secondly, a method of manufacturing absorbent articles according to one or more embodiments will be explained with reference to FIG. 2 which is a diagram for explaining a relevant part of the absorbent article manufacturing method.

Figure 2:
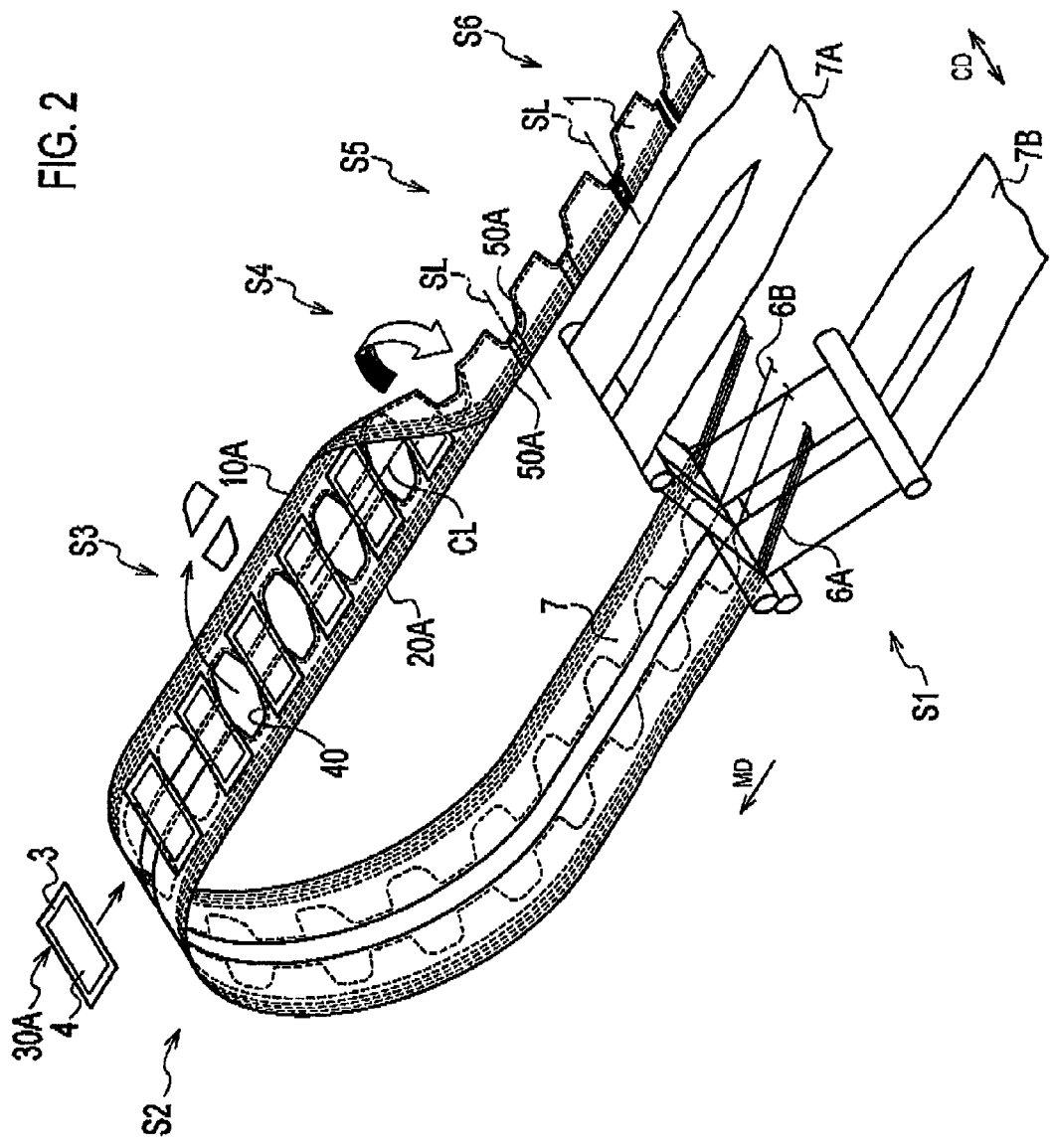
FIG. 2 is a diagram for explaining a relevant part of a method of manufacturing absorbent articles according to one or more embodiments.

As shown in FIG. 2, the method of manufacturing absorbent articles includes at least a waistline forming step S1, an absorber transferring step S2, a leg-surrounding opening forming step S3, a folding step S4, a joining step S5 and a cutting step S6.

In the waistline forming step S1, gathers (a waist gather 6A and/or a leg gather 6B) are placed between a web 7A and a web 7B, and thereby a web 7 prepared to form the front waistline portion 10 and the back waistline portion 20 is formed.

Note that the web 7 (webs 7A, 7B) during conveyance is stretchable in a cross direction CD (width direction) perpendicular to a conveyance direction MD (machine direction) of the web 7. In addition, the web 7 is asymmetrical with respect to a center line CL that bisects a width in the cross direction CD of the web 7 and extends in the conveyance direction MD of the web 7.

In the absorber transferring step S2, a crotch portion member 30A to form the crotch portion 30 is transferred onto the web 7, more specifically, between the front waistline portion 10 and the back waistline portion 20 after the waistline forming step S1. Here, the crotch portion member 30A includes the back sheet 3 and the absorber 4.

In the leg-surrounding forming step S3, the leg-surrounding openings 40 (so-called leg holes) are formed by cutting the web 7 (webs 7A, 7B) after the absorber transferring step S2. Here, the formation of the leg-surrounding opening 40 does not necessarily involve cutting only the web 7A and the web 7B, but may involve cutting, together with the web 7A and the web 7B, the back sheet 3 constituting the crotch portion member 30A.

Note that the absorber transferring step S2 and the leg-surrounding forming step S3 may be performed in the reverse order.

In the folding step S4, the web 7 is folded into two parts along a folding line extending in the conveyance direction MD of the web 7 by bringing a side edge portion 10A of the front waistline portion 10 toward a side edge portion 20A of the back waistline portion 20, after the leg-surrounding forming step S3.

Note that, in this particularly illustrated embodiment, the folding line is the center line CL. However, the folding line is not necessarily the center line CL, and may be shifted from the center line CL toward either of the side edge portion 10A and the side edge portion 20A.

In the joining step S5, the folded parts of the web 7 are joined together in joint regions 50A, through ultrasonic treatment or heat treatment after the folding step S4. The joint region 50A extends, in the conveyance direction MD, across an imaginary line SL that indicates a to-be-cut position and extends in the cross direction CD of the web 7.

In the cutting step S6, the web 7 joined in the joint regions 50A is cut along the imaginary lines SL after the joining step S5. Thereby, the absorbent article 1 is manufactured.

Next, a method of manufacturing the above-described absorber 4 will be explained with reference to FIG. 3 which is a diagram for explaining a relevant part of the absorber manufacturing method.

Here, the absorber 4 is formed of an absorber core and a cover material. The absorber core includes a first absorber core 4A and a second absorber core 4B.

The first absorber core 4A is made of ground pulp, superabsorbent polymer (SAP), and the like. The second absorber core 4B is made of ground pulp, hydrophilic fiber (fabric), absorbent gel, and the like.

Figure 3:
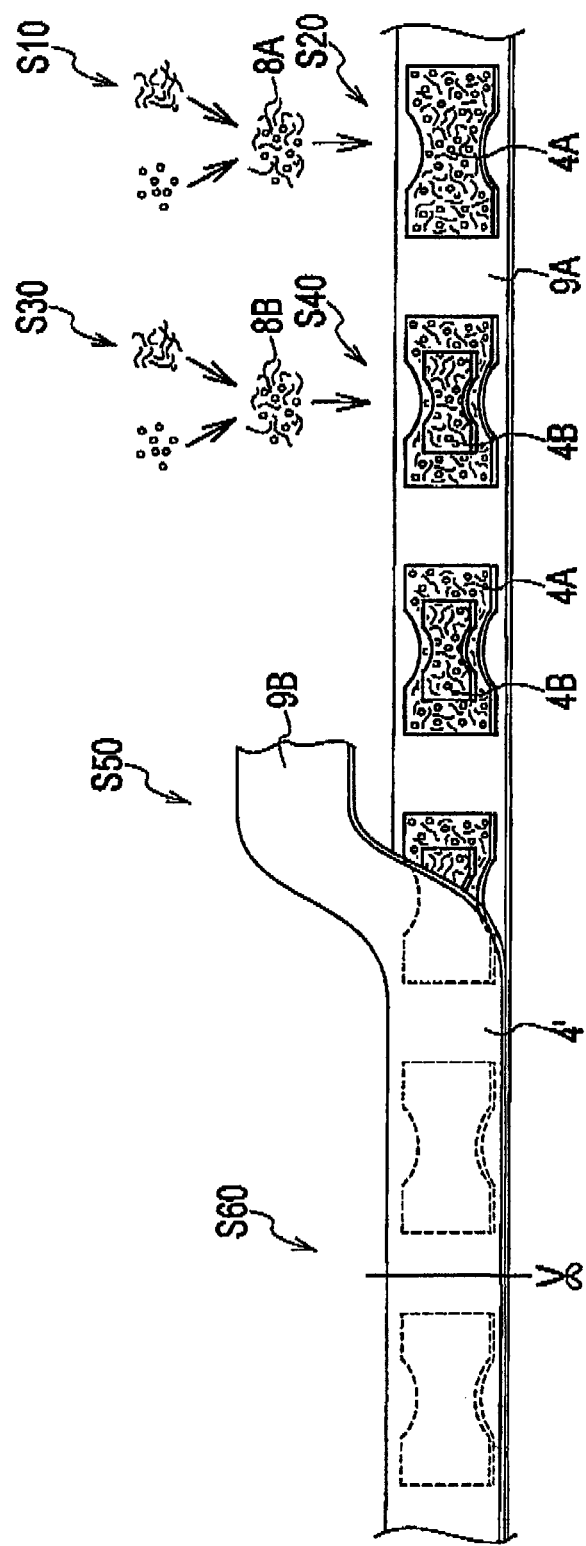
FIG. 3 is a diagram for explaining a relevant part of an absorber manufacturing method according to one or more embodiments.

The cover material covers the first absorber core 4A and the second absorber core 4B stacked on each other (see FIG. 3). The cover material includes webs 9A, 9B formed of tissue and the like.

As shown in FIG. 3, the method of manufacturing the absorber 4 thus configured includes at least a first powder mixture making step S10, a main body forming and placing step S20, a second powder mixture making step S30, a core forming and placing step S40, a web joining step S50, and a web cutting step S60.

In the first powder mixture making step S10, ground pulp is prepared by grinding a pulp sheet with a grinder. Subsequently, the ground pulp is mixed with superabsorbent polymer while passing through a supply duct, and thereby a first powder mixture 8A (first powder) is made.

In the core forming and placing step S20, an absorber forming and transferring mechanism 100 (a lamination drum 140) to be described later forms the first absorber cores 4A by collecting the first powder mixture 8A, and places the first absorber cores 4A on a web 9A, being conveyed and including cover materials, at predetermined intervals in the conveyance direction MD of the web 9A.

In the second powder mixture making step S30, ground pulp is prepared by grinding a pulp sheet with the same or a different grinder. Subsequently, the ground pulp is mixed with hydrophilic fiber and absorbent gel while passing through a supply duct, and thereby a second powder mixture 8B (second powder) is made.

In the core forming and placing step S40, the absorber forming and transferring mechanism 100 (a forming drum 150 and a rotary transfer member 160) to be described later forms the second absorber cores 4B by collecting the second powder mixture 8B, and places the second absorber cores 4B on the first absorber cores 4A that have been placed on the web 9A, at predetermined intervals in the conveyance direction MD of the web 9A.

In the web joining step S50, a web 9B including cover materials is overlaid on the web 9A with the first absorber cores 4A and the second absorber cores 4B stacked thereon.

In the web cutting step S60, while being conveyed, e.g., by rotation of a rotary drum, a continuous absorber web 4' formed of the webs 9A, 9B with the absorber cores interposed therebetween is cut in the cross direction CD perpendicular to the conveyance direction MD of the absorber web 4' at predetermined intervals, e.g., by a cutter roll placed to face the outer circumference surface of the rotary drum. Thereby, the absorbers 4 are manufactured.

Figure 4:
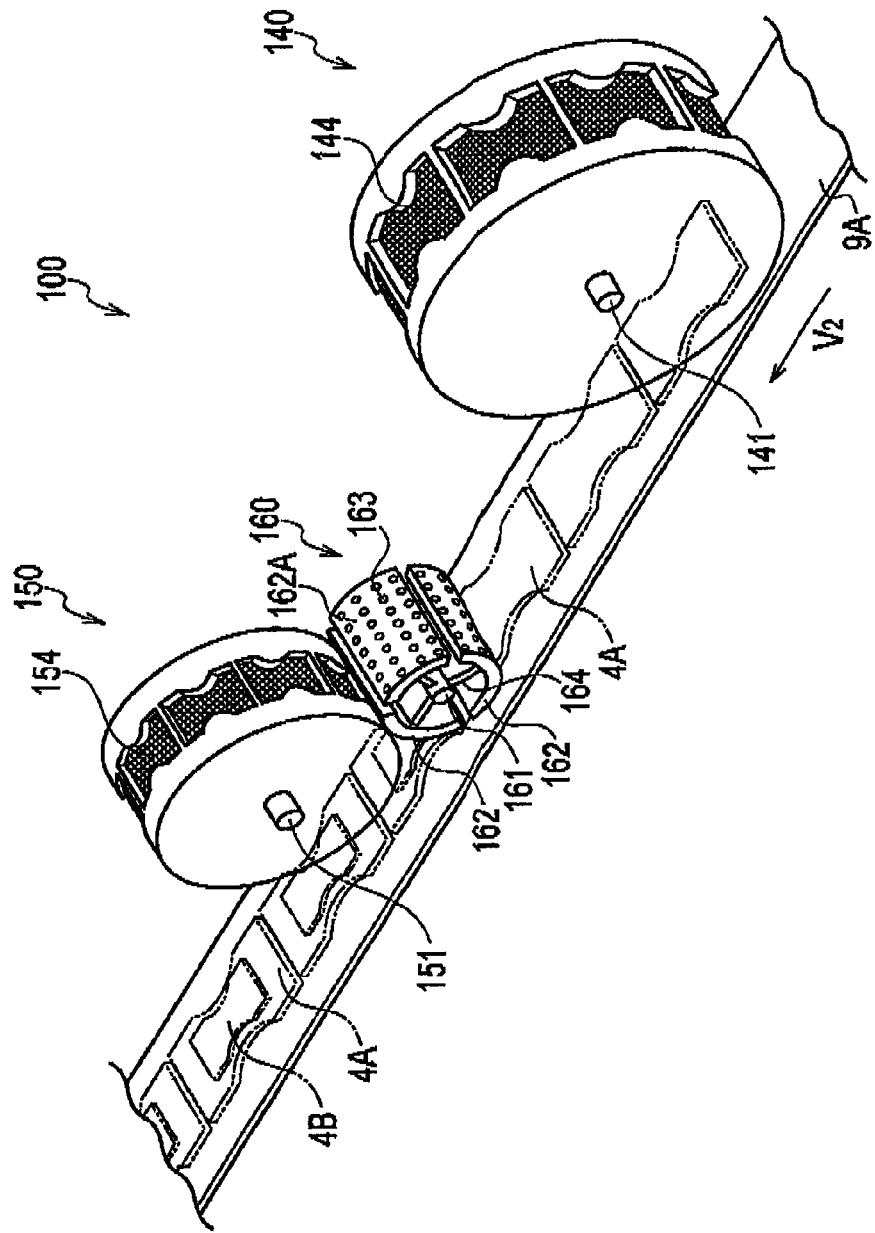
FIG. 4 is a perspective view of an absorber forming and transferring mechanism according to one or more embodiments.
Figure 5:
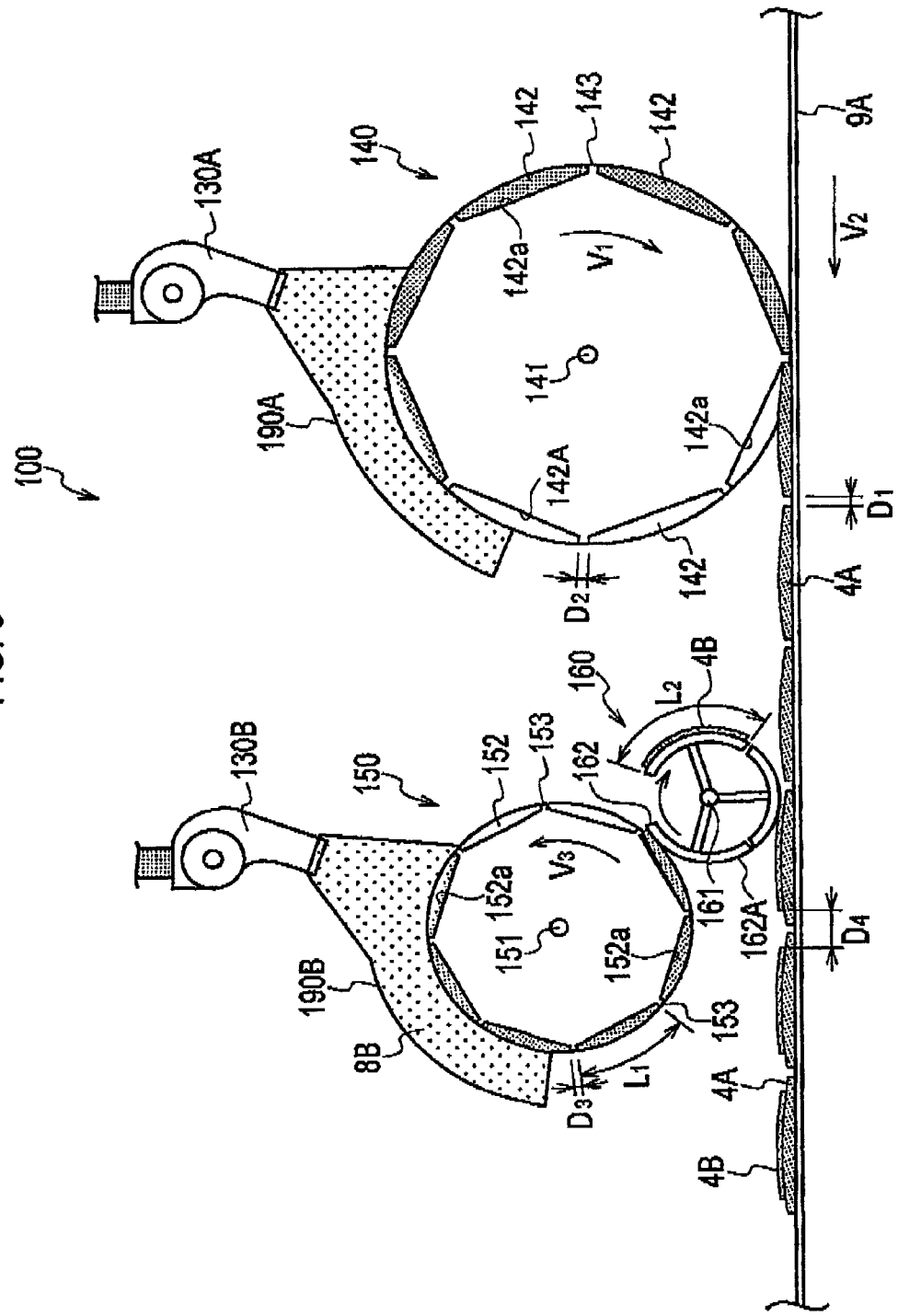
FIG. 5 is a side view of the absorber forming and transferring mechanism of FIG. 4.
Figure 6:
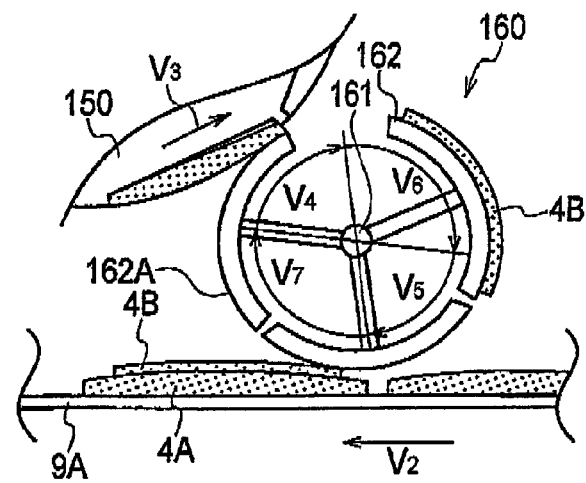
FIG. 6 is an enlarged side view of a rotary transfer member of the absorber forming and transferring mechanism of FIG. 5.
Figure 7:
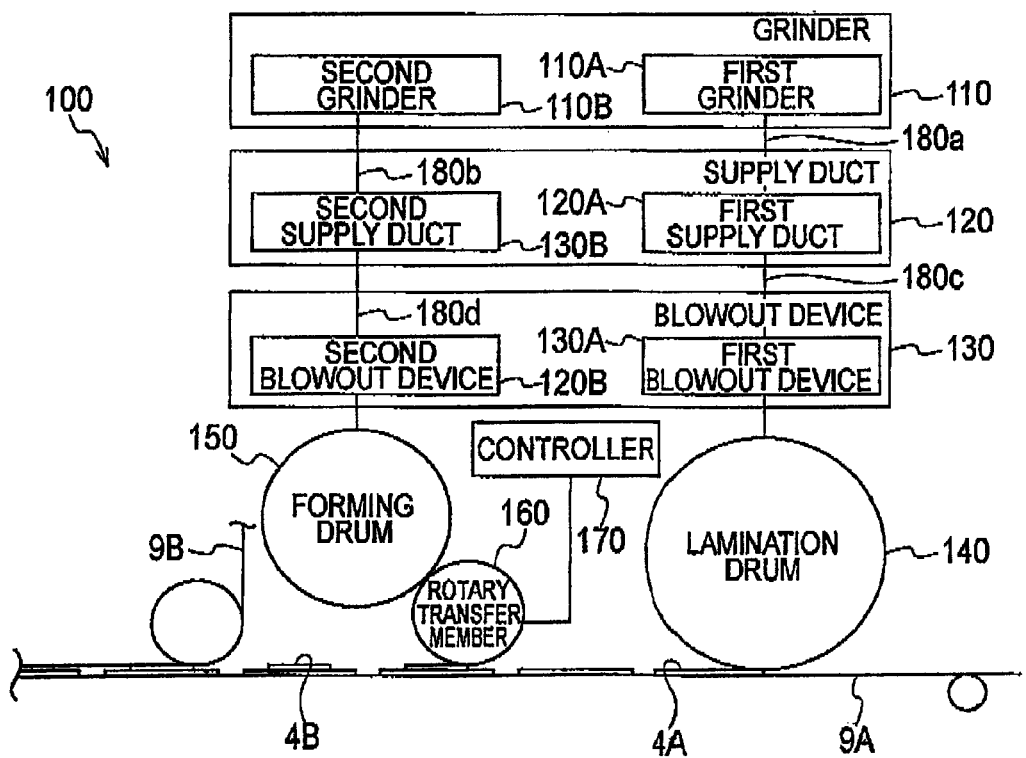
FIG. 7 is a block diagram of the absorber forming and transferring mechanism according to one or more embodiments.

Next, a configuration of the absorber forming and transferring mechanism 100 used for manufacturing the above-described absorber 4 in accordance with one or more embodiments will be explained with reference to FIGS. 4-7. FIG. 4 is a perspective view of the absorber forming and transferring mechanism 100. FIG. 5 is a side view of the absorber forming and transferring mechanism 100. FIG. 6 is an enlarged side view of a rotary transfer member 160 of the absorber forming and transferring mechanism 100. FIG. 7 is a block diagram of the absorber forming and transferring mechanism 100.

As shown in FIGS. 4 to 7, the absorber forming and transferring mechanism 100 includes a grinder 110, a supply duct 120, a blowing device 130, the lamination drum 140, the forming drum 150, the rotary transfer member 160, and a controller 170.

The grinder 110 includes a first grinder 110A and a second grinder 110B. The first grinder 110A is positioned at the side of the lamination drum 140. The second grinder 110B is positioned at the side of the forming drum 150. The first grinder 110A and the second grinder 110E grind pulp sheets to form ground pulp.

The supply duct 120 includes a first supply duct 120A and a second supply duct 120B. The first supply duct 120A is connected to the first grinder 110A through a supply pipe 180a. The first supply duct 120A supplies (adds) superabsorbent polymer to ground pulp, and thereby forms the first powder mixture 8A. The second supply duct 120B is connected to the second grinder 110E through a supply pipe 180b. The second supply duct 120B supplies hydrophilic fiber and absorbent gel to ground pulp, and thereby forms the second powder mixture 8B.

The blowing device 130 includes a first blowing device 130A and a second blowing device 130B. The first blowing device 130A is connected to the first supply duct 120A through a supply pipe 180c, and to the lamination drum 140 through an introducing guide 190a. The first blowing device 130A blows the first powder mixture 8A toward the lamination drum 140. The second blowing device 130B is connected to the second supply duct 120B through a supply pipe 180d, and to the forming drum 150 through an introducing guide 190b. The second blowing device 130B blows the second powder mixture 8B toward the forming drum 150.

The first powder mixture 8A and the second powder mixture 8B are blown with air through the supply pipes 180a, 180c and the supply pipes 180b, 180d by unillustrated fans or the like.

While rotating about a shaft 141, the lamination drum 140 forms the first absorber core 4A from the first powder mixture 8A blown out from the first blowing device 130A. Moreover, the lamination drum 140 places the first absorber cores 4A on the web 9A at predetermined intervals $D_1$ prior to the second absorber cores 4B.

The lamination drum 140 is provided upstream of the forming drum 150 and the rotary transfer member 160 in the conveyance direction MD of the web 9A. The rotational velocity $V_1$ of the lamination drum 140 is equal to the conveyance velocity $V_2$ of the web 9A. In this case, the rotational velocity $V_1$ of the lamination drum 140 within a difference of ±5% from the conveyance velocity $V_2$ of the web 9A is regarded as equal to the conveyance velocity $V_2$. As used herein, two velocities are considered equal if their difference is within ±5%.

The lamination drum 140 has a larger diameter than the forming drum 150. Main body forming recesses 142 that form the first absorber cores 4A by collecting the first powder mixture 8A therein are formed at predetermined intervals $D_2$ in the outer circumference surface of the lamination drum 140. In other words, portions other than the main body forming recesses 142 on the outer circumference surface of the placement drum 142 are convex portions 143 projecting from the main body forming recesses 142.

It is preferable in some embodiments to make the predetermined interval $D_2$ between the main body forming recesses 142 (namely, the size of each of the convex portions 143) small so as to prevent an excessive amount of the first powder mixture 8A from adhering to the convex portions 143 and being wasted. Since the rotational velocity $V_1$ of the lamination drum 140 is equal to the conveyance velocity $V_2$ of the web 9A, the predetermined interval $D_2$ between the main body forming recesses 142 is equal to the predetermined interval $D_1$ between the first absorber cores 4A placed on the web 9A.

A bottom portion 142a, positioned closest to the shaft 141, of each of the main body forming recesses 142 is a flat surface. The bottom portion 142a is provided with multiple suction holes 144 (FIG. 4) arranged in a mesh pattern and configured to attract the first powder mixture 8A.

While rotating about a shaft 151, the forming drum 150 forms the second absorber core 4B from the second powder mixture 8B blown out from the second blowing device 130B. Here, the second absorber core 4B is smaller in size than the first absorber core 4A. Moreover, the forming drum 150 passes the second absorber core 4B to the rotary transfer member 160.

The rotational velocity $V_3$ of the forming drum 150 is equal to or lower than the conveyance velocity $V_2$ of the web 9A. The forming drum 150 has a smaller diameter than the lamination drum 140.

Forming recesses 152 that form the second absorber cores 4B by collecting the second powder mixture 8B therein are formed at predetermined intervals $D_3$ in the outer circumference surface of the forming drum 150. In other words, portions other than the forming recesses 152 on the outer circumference surface of the forming drum 150 are convex portions 163 projecting from the forming recesses 152. Each of the predetermined intervals $D_3$ between the multiple forming recesses 152 (namely, the length of each of the convex portions 153) is narrower than the length $L_1$ of the forming recess 152 when viewed in an axis direction of the forming drum 150.

A bottom portion 152a of each of the forming recesses 152 is a flat surface. The bottom portion 152a is provided with multiple suction holes 154 (FIG. 4) arranged in a mesh pattern and configured to attract the second powder mixture 8B.

While rotating about a shaft 161, the rotary transfer member 160 receives the second absorber cores 4B, formed by the forming drum 150, from the forming drum 150, and transfers the second absorber cores 4B received from the forming drum 150 onto the web 9A. More specifically, the rotary transfer member 160 transfers the second absorber cores 4B onto the first absorber cores 4A that have been placed on the web 9A prior to the second absorber cores 4B.

Note that an interval $D_4$ of two adjacent second absorber cores 4B placed on the first absorber cores 4A is wider than the predetermined interval $S_1$ between the first absorber cores 4A placed on the web 9A.

The rotary transfer member 160 is provided between the forming drum 150 and the web 9A. The rotary transfer member 160 includes multiple (three in the drawing) suction pads 162 each for attracting one second absorber core 4B at a time. When viewed in an axis direction of the rotary transfer member 160, the length $L_2$ of each of the suction pads 162 is equal to the length $L_1$ of the forming recess 152, namely the length of the second absorber core 4B.

Multiple air nozzles 163 (FIG. 4) are formed in the suction pad 162. The air nozzles 163 are connected to an air source (not shown) through a coupling portion 164 joined to the shaft 161. The suction pad 162 includes a holding surface 162A for attracting the second absorber core 4B. The holding surface 162A has an arc shape extending in a rotation direction of the rotary transfer member 160.

The suction pads 162 are rotatable about a common rotational axis (shaft 161) independently of each other, so that at a given point in time, one suction pad 162 may rotate faster (or slower) than the other suction pads. Each suction pad 162 rotates at different rotational velocities during one rotation of the rotary transfer member 160.

Specifically, as shown in FIG. 6, the rotational velocity $V_4$ of the suction pad 162 is equal to the rotational velocity $V_3$ of the forming drum 150 at the time when the suction pad 162 receives the second absorber core 4B from the forming drum 150 (hereinafter, referred to as the core reception time). The rotational velocity $V_5$ of the suction pad 162 is equal to the conveyance velocity $V_2$ of the web 9A at the time when the suction pad 162 transfers the second absorber core 42 onto the web 9A (hereinafter, referred to as the core transfer time).

The rotational velocity $V_6$ of the suction pad 162 is higher than the rotational velocity $V_3$ of the forming drum 150 during a period from the core reception time to the core transfer time. The rotational velocity $V_7$ of the suction pad 162 is lower than the conveyance velocity $V_2$ of the web 9A during a period from the core transfer time to the core reception time.

The controller 170 controls the rotational velocities $V_4$ to $V_7$. In this embodiment, as described above, the rotational velocity $V_1$ of the lamination drum 140 is set equal to the conveyance velocity $V_2$ of the web 9A, and the rotational velocity $V_3$ of the forming drum 150 is set equal to or lower than the conveyance velocity $V_2$ of the web 9A.

The controller 170 controls the rotational velocity $V_4$ of each suction pad 162 of the rotary transfer member 160 so that the velocity $V_4$ should be equal to the rotational velocity $V_3$ of the forming drum 150 at the core reception time. Moreover, the controller 170 controls the rotational velocity $V_5$ of each suction pad 162 of the rotary transfer member 160 so that the velocity $V_5$ should be equal to the conveyance velocity $V_2$ of the web 9A at the core transfer time.

In other words, as shown in FIG. 5, the velocity $V_1$ of the lamination drum 140 is equal to the conveyance velocity $V_2$ of the web 9A. The rotational velocity $V_3$ of the forming drum 150 is equal to or slower than the conveyance velocity $V_2$. In other words, the controller 170 controls the rotation velocity of the rotary transfer member 160 so that $V_1=V_2 \geq V_3$.

In addition, the controller 170 causes the rotational velocity $V_6$ of each suction pad 162 of the rotary transfer member 160 to be higher than the rotational velocity $V_3$ of the forming drum 150 during a period from the core reception time to the core transfer time. Moreover, the controller 170 causes the rotational velocity $V_7$ of each suction pad 162 of the rotary transfer member 160 to be lower than the conveyance velocity $V_2$ of the web 9A.

In the embodiment described thus far, the rotational velocity $V_4$ of each suction pad 162 of the rotary transfer member 160 is equal to the rotational velocity $V_3$ of the forming drum 150 at the core reception time ($V_4=V_3$). This velocity setting enables each suction pad 162 of the rotary transfer member 160 to smoothly receive the second absorber core 4B from the forming drum 150, and thus prevents a crease or the like from occurring in the second absorber core 4B. In contrast, if the rotational velocity $V_4$ of each suction pad 162 of the rotary transfer member 160 is different from the rotational velocity $V_3$ of the forming drum 150 at the core reception time, a crease or the like may occur in the second absorber core 4B and the mass per unit area or the like tends to vary in the second absorber core 4B.

Meanwhile, the rotational velocity $V_5$ of each suction pad 162 of the rotary transfer member 160 is equal to the conveyance velocity $V_2$ of the web 9A at the core transfer time ($V_5=V_2$). This velocity setting enables each suction pad 162 of the rotary transfer member 160 to smoothly place the second absorber core 4B on the first absorber core 4A placed on the web 9A. Thereby, a crease or the like can be prevented from occurring in the second absorber core 4B. In contrast, if the rotational velocity $V_5$ of each suction pad 162 of the rotary transfer member 160 is different from the conveyance velocity $V_2$ of the web 9A at the core transfer time, a crease or the like may occur in the second absorber core 4B, and the mass per unit area or the like tends to vary in the second absorber core 4B.

The rotational velocity $V_6$ of each suction pad 162 of the rotary transfer member 160 is higher than the rotational velocity $V_3$ of the forming drum 150 during the period from the core reception time to the core transfer time (i.e., $V_6 > V_3 = V_4$). The rotational velocity $V_7$ of each suction pad 162 of the rotary transfer member 160 is lower than the conveyance velocity $V_2$ of the web 9A during a period from the core transfer time to the core reception time (i.e., $V_7 < V_2 = V_5$). Such velocity settings enable the predetermined interval $D_3$ between the forming recesses 152 (namely, the size of the convex portion 153) to be set small so as to prevent an excessive amount of the second powder mixture BB from adhering to the portions other than the forming recesses 152 on the outer circumference surface of the forming drum 150 (namely, to the convex portions 153). Accordingly, even if the predetermined interval $D_3$ between the forming recesses 152 is narrow, the interval $D_4$ (see FIG. 5) between the second absorber cores 4B placed on the first absorber cores 4A can be widened. In other words, the intervals $D_4$ of the second absorber cores 4B placed on the first absorber cores 4A can be appropriately set in accordance with the predetermined intervals $D_1$ of the first absorber cores 4A. Therefore, the second powder mixture 8B is not much wasted, and hence the cost of manufacturing the absorber 4 can be surely saved.

Here, consider a case where the rotary transfer member 160 is not provided. In this case, the predetermined interval $D_3$ between the multiple forming recesses 152 needs to be widened (i.e., the convex portion 153 needs to be made large) in order to widen the interval $D_4$ between the second absorber cores 4B placed on the web 9A. As a result, the second powder mixture 8B adhered to the convex portion 153 is deposited in the forming recess 152 positioned behind the convex portion 153 in the rotation direction of the forming drum 150. Thereby, the mass per unit area or the like tend to vary in the second absorber core 4B.

In contrast, if the predetermined interval $D_3$ between the multiple forming recesses 152 is narrowed, the interval $D_4$ between the second absorber cores 4B placed on the web 9A is also narrowed. In order to widen the interval $D_4$ to place the second absorber cores 4B, the rotational velocity $V_3$ of the forming drum 150 needs to be made higher than the conveyance velocity $V_2$ of the web 9A. In this case, the second absorber cores 4B are placed on the first absorber cores 4A in a stretched state. In this case, the second absorber core 4B is not always stretched evenly, and thus is formed with unevenness.

To address these issues, in this embodiment as described above, the interval $D_4$ between the second absorber cores 4B placed on the first absorber cores 4A can be set appropriately. Therefore, the second powder mixture 8B is not much wasted, and hence the cost of manufacturing the absorber 4 can be surely saved.

If the second absorber core 4B larger than the first absorber core 4A is placed on the first absorber core 4A, the second absorber core 4B is stretched at a portion protruding from the first absorber core 4A. Specifically, the second absorber core 4B protruding from the first absorber core 4A is deformed in accordance with the shape of the first absorber core 4A by gravity and the like. Especially, a boundary portion where the second absorber core 4B protrudes from the first absorber core 4A is deformed. In this way, the second absorber core 4B is easily deformed, and thus is unevenly placed on the first absorber core 4A.

To address this issue, in this embodiment, the second absorber core 4B is made to be smaller than the first absorber core 4A. Thereby, the second absorber cores 4B are not easily deformed, and hence are evenly placed.

In this embodiment, multiple suction holes 154 are provided in the bottom portion 152a of each of the forming recesses 152. Thereby, the second powder mixture 8B is easily collected in the forming recess 152. Therefore, the second powder mixture 8B does not easily adhere to the portions other than the forming recesses 152 on the outer circumference surface of the forming drum 150 (namely, on the convex portions 153) when the second absorber cores 4B are formed.

In this embodiment, the bottom portion 152a of the forming recess 152 has a flat surface. For example, in order to form the absorber 4 including portions of different thicknesses without using the lamination drum 140, the bottom portion 152a of the forming recess 152 needs to be provided with steps. However, if the steps are formed in the bottom portion 152a, the second powder mixture 8B is deposited unevenly at the steps due to changes in suction pressure and/or physical shape, and thereby the second absorber core 4B is formed with unevenness. To avoid this issue, the bottom portion 152a having a flat surface allows the second powder mixture 8B to be collected evenly in the forming recess 152, and thus prevents the second absorber core 48 from being made uneven.

In this embodiment, the predetermined interval $D_3$ between the multiple forming recesses 152 (namely, the length of the convex portion 153) is narrower than the length $L_1$ of the forming recess 152 when viewed in the axis direction of the forming drum 150. This prevents the second powder mixture SB from excessively adhering to the convex portions 153. Therefore, the second powder mixture 8B adhered to the convex portion 153 is prevented from being deposited in the forming recess 152 positioned behind the convex portion 153 in the rotation direction of the forming drum 150, which in turn prevents the mass per unit area from varying in the second absorber core 4B.

In this embodiment, the length $L_2$ of the suction pad 162 is equal to the length $L_1$ of the forming recess 152, namely the length of the second absorber core 4B, when viewed in the axis direction of the rotary transfer member 160. The holding surface 162A has an arc shape extending in the rotation direction of the rotary transfer member 160 when viewed in the axis direction of the rotary transfer member 160. This configuration allows the rotary transfer member 160 to smoothly receive the second absorber core 43 from the forming drum 150, and to smoothly place the second absorber core 4B on the first absorber core 4A placed on the web 9A, compared with a case where the holding surface 162A is a flat surface. Therefore, a crease or the like can be surely prevented from occurring in the second absorber core 43.

Modified Examples

Figure 8:
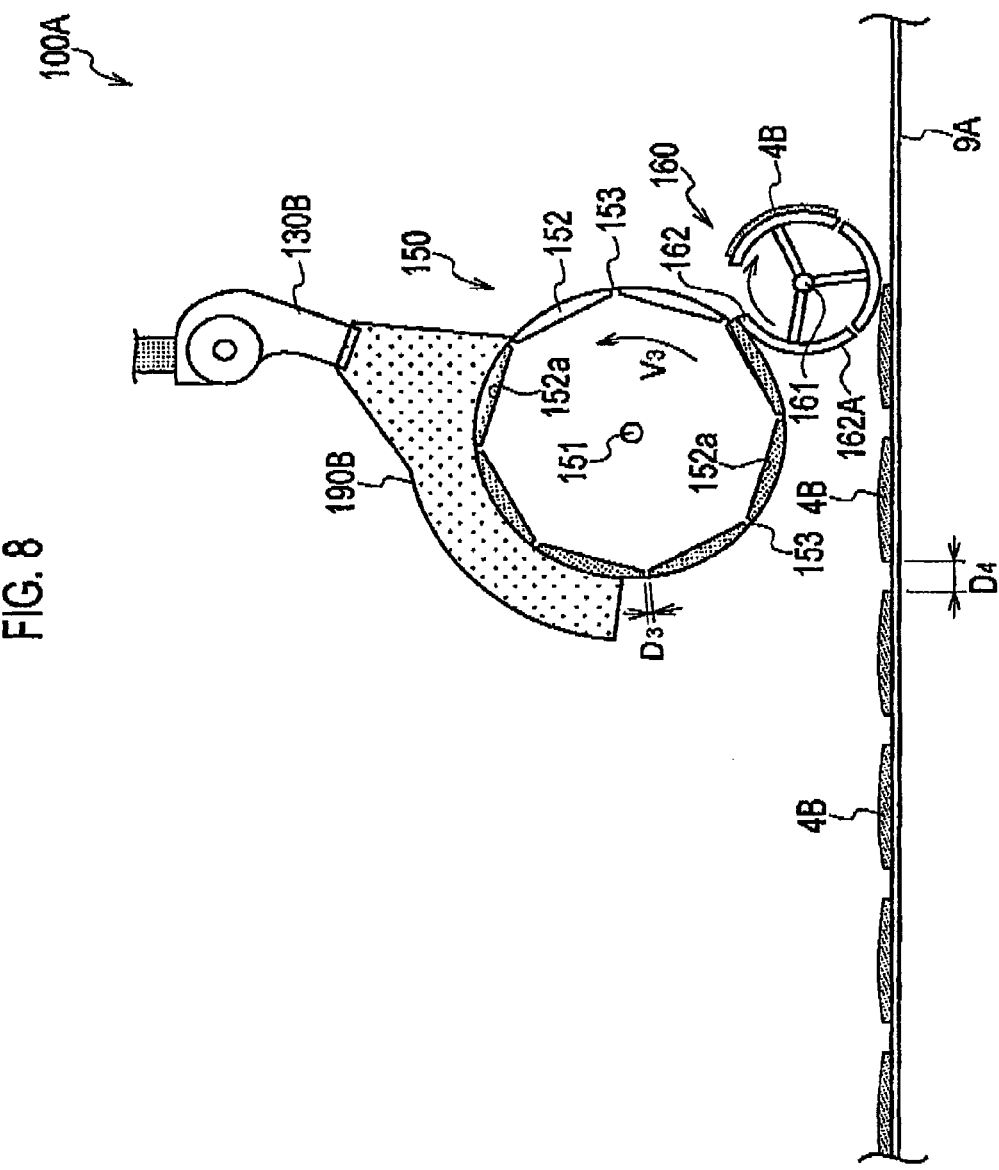
FIG. 8 is a side view of an absorber forming and transferring mechanism according to one or more modified embodiments.

The absorber forming and transferring mechanism 100 according to the foregoing description may be modified as follows. FIG. 8 is a side view of an absorber forming and transferring mechanism 100A according to one or more modified embodiment. Here, description will be provided mainly for differences from the foregoing description, with the same or similar reference signs denoting the same or similar elements.

The absorber core manufactured by the absorber forming and transferring mechanism 100 as described above is formed of the first absorber core 4A and the second absorber core 4B. In contrast, an absorber core manufactured by the absorber forming and transferring mechanism 100A is formed of the second absorber core 4B only. In other words, the absorber forming and transferring mechanism 100A does not include the lamination drum 140. Accordingly, the absorber forming and transferring mechanism 100A does not include the first grinder 110A or the first supply duct 120A.

The modified embodiment(s) is capable of achieving the same advantageous effect(s) as described above in that the predetermined interval $D_3$ between the forming recesses 152 (namely, the size of the convex portion 153) can be set small so as to prevent an excessive amount of the second powder mixture 8B from adhering to portions other than the forming recesses 152 on the outer circumference surface of the forming drum 150 (namely, to the convex portions 153). Accordingly, even if the predetermined interval $D_3$ between the forming recesses 152 is narrow (i.e., even if the rotational velocity of the rotary transfer member 160 is high), the interval $D_4$ between the second absorber cores 4B placed on the web 9A can be widened, in other words, the interval $D_4$ between the second absorber cores 4B placed on the web 9A can be set appropriately. Therefore, the second powder mixture 8B is not much wasted, and hence the cost of manufacturing the absorber 4 can be surely saved.

Further Embodiments

As described above, the details of several embodiments of the present invention have been exemplarily disclosed. It should not be understood that the description and drawings which constitute part of this disclosure limit the present invention. Based on this disclosure, those skilled in the art may easily come up with various alternative embodiments, examples and operation techniques.

For, example, the following additional embodiments can be envisaged. Specifically, the absorbent article 1 has been described as including, in combination, the front waistline portion 10, the back waistline portion 20 and the crotch portion 30. The absorbent article 1 is not limited to this configuration, but may be formed entirely as a single unit. In this case, needless to say, a different method of manufacturing an absorbent article is employed.

Additionally, the absorber forming and transferring mechanism has been described as being configured for manufacturing and transferring absorber cores for making disposable diapers. However, the absorber forming and transferring mechanism is not limited to this use. For example, the absorber forming and transferring mechanism in some embodiments may manufacture and transfer absorber cores for making sanitary napkins and/or panty liners. In further embodiments, the absorber forming and transferring mechanism may be used for transferring other components, not necessarily absorbent cores.

Moreover, the first powder mixture 8A and the second powder mixture 8B have been described as being made of different materials. However, the powder mixtures 8A and 8B are not limited to these ingredients. The powder mixtures 8A and 8B may each be made of one material (for example, ground pulp only or superabsorbent polymer only), or of more than one, e.g., two or more, materials.

In addition, the controller 170 has been described as being configured for controlling the rotational velocities $V_4$ to $V_7$ of the suction pads 162 of the rotary transfer member 160. However, the controller 170 is not limited to this role. The controller 170 may control the rotational velocity $V_1$ of the lamination drum 140, the rotational velocity $V_3$ of the forming drum 150, the conveyance velocity $V_2$ of the web 9A, or the like.

Further, the bottom portion 152a of the forming recess 152 has been described as having a flat surface. However, the bottom portion 152a is not limited to this structure, and may have a surface other than a flat surface. For example, the bottom portion 152a may have a curved surface convex away from the shaft 151 of the forming drum 150, or may have a curved surface concave toward the shaft 151. In an exemplary embodiment, the bottom portion 152a is curved to be coaxial with the outer circumference surface of the forming drum 150), when viewed in the axis direction of the forming drum 150.

Additionally, the rotational velocity $V_3$ of the forming drum 150 has been described as being equal to or lower than the conveyance velocity $V_2$ of the web 9A. However, the rotational velocity $V_3$ is not limited to this velocity, and may be'higher than the conveyance velocity $V_2$ of the web 9A. As used herein, one velocity (rotational and/or conveyance velocity) is considered greater than another if their difference is greater than ±5%.

Moreover, the lamination drum 140 has been described as having a larger diameter than the forming drum 150. However, the lamination drum 140 is not limited to this structure, and may have a diameter equal to or smaller than the forming drum 150.

In addition, the descriptions have been given for the multiple suction holes 144 provided in the bottom portion 142a of the lamination drum 140 and for the multiple suction holes 154 provided in the bottom portion 152a of the forming drum 150. However, the bottom portions 142a and 152a are not limited to this configuration, and may be provided with no suction holes.

Further, the rotary transfer member 160 has been described as including multiple suction pads 162. However, the rotary transfer member 160 is not limited to this structure, and may, for example, include a single suction pad or be a rotary drum (roller) which is controlled to rotate at various velocities $V_4$-$V_7$ as described herein. In this case, suction holes for attracting the second powder mixture 8B to form the second absorber cores 4B are formed in a mesh pattern in the outer circumference surface of the rotary drum.

Additionally, the length $L_2$ of the suction pad 162 has been described as being equal to the length $L_1$ of the forming recess 152, namely the length of the second absorber core 4B, when viewed in the axis direction of the rotary transfer member 160. However, the length $L_2$ is not limited to this, and may be larger than length $L_1$ of the forming recess 152, for example.

As described above, the present invention naturally includes various embodiments which are not described herein. Accordingly, the technical scope of the present invention should be determined only by the matters to define the invention in the scope of claims regarded as appropriate based on the description.

The entire contents of Japanese Patent Applications 2009-048402 (filed on Mar. 2, 2009) and 2010-041922 (filed on Feb. 26, 2010) are incorporated herein by reference.

Industrial Applicability

Therefore, according to the present invention, since it is possible to provide the absorber forming and transferring mechanism and a method of manufacturing an absorbent article, which allow a predetermined interval between absorber cores placed on a web to be appropriately set in a case where the absorber cores are placed on the web at the predetermined intervals and achieve saving cost for manufacturing an absorber, it is useful in manufacturing technology for absorbent articles.

REFERENCE SIGNS LIST 1 absorbent article
2 top sheet
3 back sheet
4 absorber
4' absorber web
4A first absorber core
4B second absorber core
5 waterproof sheet
6A waist gather
6B leg gathers
7, 7A, 7B web
8A first powder mixture
8B second powder mixture
9A, 9B web
10 front waistline portion
10A side edge portion
20 back waistline portion
20A side edge portion
30 crotch portion
40 leg-surrounding openings
50 joint portion
50A joint region
60 body-surrounding openings
100, 100A absorber forming and transferring mechanism
110 grinder
120 supply duct
130 blowing device
140 lamination drum
142 main body forming recess
150 forming drum
160 rotary transfer member
161 shaft core
162 suction pad
162A holding surface
163 air nozzles
164 coupling portion
170 controller

The invention claimed is:

1. A mechanism for manufacturing an absorber including absorber cores and a cover material covering the absorber cores, the mechanism comprising:
a lamination drum configured to form a first absorber core by collecting power and to place the first absorber core on a web defining a continuum of the cover material,
a forming drum having forming recesses made at predetermined intervals, and configured to form a second absorber core by collecting the powder;
a rotary transfer member configured to receive from the forming drum the second absorber core formed by the forming drum, and to transfer the second absorber core received from the forming drum onto the web having the first absorber core placed thereon; and
a controller for controlling a rotational velocity of the rotary transfer member to equalize a velocity of the forming drum and a velocity of the traveling web at a core reception time and at a core transfer time.

2. The mechanism according to claim 1, wherein the controller is configured for controlling the rotational velocity of the rotary transfer member to be equal to the velocity of the forming drum at the core reception time.

3. The mechanism according to claim 1, wherein the controller is configured for controlling the rotational velocity of the rotary transfer member to be equal to the velocity of the traveling web at the core transfer time.

4. The mechanism according to claim 3, wherein the controller is configured
for adjusting the rotational velocity of the rotary transfer member from the velocity of the forming drum to the velocity of the traveling web during a first period from the core reception time to the core transfer time, and
for adjusting the rotational velocity of the rotary transfer member from the velocity of the traveling web to the velocity of the forming drum during a second period from the core transfer time to the core reception time.

5. The mechanism according to claim 3, wherein the controller is configured for
causing the rotational velocity of the rotary transfer member to be higher than the velocity of the forming drum during a first period from the core reception time to the core transfer time, and
causing the rotational velocity of the rotary transfer member to be lower than the velocity of traveling web during a second period from the core transfer time to the core reception time.

6. The mechanism according to claim 1, wherein the rotary transfer member includes a plurality of suction pads each attracting the absorber core.

7. The mechanism according to claim 1, wherein
the rotary transfer member includes a plurality of suction pads each for holding one of the absorber cores received from the forming drum at a time.

8. The mechanism according to claim 6, wherein a length of each of the suction pads is equal to a length of each of the forming recesses, when viewed in an axis direction of the rotary transfer member.

9. The mechanism according to claim 1, wherein a bottom portion of the forming recess has a flat surface.

10. The mechanism according to claim 1, wherein the predetermined interval between the forming recesses is narrower than a length of each of the forming recesses, when viewed in an axis direction of the forming drum.

11. A method of manufacturing an absorber for an absorber article, the method comprising:
collecting powder to form a first absorber core for the absorber;
placing the first absorber core at predetermined intervals on a web being conveyed and including a cover material;
collecting powder in at least one forming recess of a forming drum to form a second absorber core;
receiving the second absorber core by a rotary transfer member and placing the second absorber core onto the web having the first absorber core placed thereon; and
controlling a rotational velocity of the rotary transfer member to equalize a velocity of the forming drum and a velocity of the travelling web at a core reception time and at a core transfer time.

12. The method according to claim 11, wherein the second absorber core is smaller than the first absorber core.

13. The method according to claim 12, wherein
the forming drum comprises a plurality of the forming recesses positioned in predetermined intervals, and
a plurality of the second absorber cores are transferred onto the web by the rotary transfer member in predetermined intervals that are greater than the predetermined intervals of forming recesses of the forming drum.

14. The mechanism according to claim 1, wherein
the laminating drum comprises at least one forming recess for collecting the power, and
the forming recess of the forming drum is smaller than the forming recess of the laminating drum such that the second absorber core is smaller than the first absorber core.

15. The mechanism according to claim 1, wherein the rotary transfer member is configured to transfer a plurality of the second absorber cores onto the web in predetermined intervals that are greater than the predetermined intervals of forming recesses of the forming drum.

* * * * *